(12) United States Patent
Santoro et al.

(10) Patent No.: US 6,660,472 B1
(45) Date of Patent: Dec. 9, 2003

(54) LYSIS METHOD FOR MICRO-ORGANISMS

(75) Inventors: Lise Santoro, Charbonnieres les Bains (FR); Sophie Lopez, Chazay d'Azergues (FR); Bruno Colin, Marcy l'Etoile (FR); Corinne Jay, Villeurbanne (FR); Cécile Paris, Marcy l'Etoile (FR); Kathleen Ann Clark Dickey, Cardiff, CA (US)

(73) Assignees: Bio Merieux, Marcy l'Etoile (FR); Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 09/509,006

(22) PCT Filed: Sep. 23, 1998

(86) PCT No.: PCT/IB98/01475

§ 371 (c)(1),
(2), (4) Date: Jul. 17, 2000

(87) PCT Pub. No.: WO99/15621

PCT Pub. Date: Apr. 1, 1999

(30) Foreign Application Priority Data

Sep. 23, 1997 (FR) .............................................. 97 12164

(51) Int. Cl.⁷ .......................... C12Q 1/68; C12P 19/34; G01N 33/00; C07H 21/02; C07H 21/00
(52) U.S. Cl. .......................... 435/6; 435/91.1; 435/91.2; 436/94; 536/23.1; 536/25.3; 536/25.4
(58) Field of Search .......................... 435/6, 91.1, 91.2, 435/183, 7.2, 7.31, 7.32; 436/94; 536/23.1, 24.3, 24.33, 25.4, 25.41, 25.3; 530/374

(56) References Cited

U.S. PATENT DOCUMENTS

| | | | |
|---|---|---|---|
| 4,295,613 A | | 10/1981 | Moore et al. |
| 4,666,850 A | | 5/1987 | Mehl et al. |
| 4,775,622 A | | 10/1988 | Hitzman et al. |
| 5,254,470 A | | 10/1993 | Murakami et al. |
| 5,399,491 A | | 3/1995 | Kacian et al. |
| 5,464,773 A | | 11/1995 | Melendez et al. |
| 5,643,767 A | * | 7/1997 | Fischetti et al. ........... 435/91.3 |
| 6,066,470 A | * | 5/2000 | Nishimura et al. ........ 435/69.1 |

FOREIGN PATENT DOCUMENTS

| EP | 0 288 618 A1 | 4/1987 |
|---|---|---|
| EP | 0317 803 A1 | 11/1987 |
| EP | 0 284 044 A1 | 3/1988 |
| EP | A1 0 284 044 | 9/1988 |
| EP | A1 0 288 618 | 11/1988 |
| EP | 0 341 215 A2 | 5/1989 |
| EP | A1 0 317 803 | 5/1989 |
| EP | A2 0 341 215 | 11/1989 |
| EP | 0 632 269 A1 | 6/1994 |
| EP | 0 770 689 A2 | 5/1997 |
| EP | 0 796 917 A2 | 9/1997 |
| FR | 1 576 299 | 7/1969 |
| FR | A1 1.576.299 | 7/1969 |

OTHER PUBLICATIONS

Hoffman et al., A ten–minute preparation from yeast efficiently releases autonomous plasmids for transformation of *Escherichia coli*. Gene, 57, 267–272, 1987.*

Lu et al., Rapid extraction of DNA from mycelia of *Fusarium graminearum* for PCR amplification. Mycosystema, 16, 36–39, Jan. 1997.*

Handbook of Chemistry and Physics, 44 edition, pp. 2189 and 2190. Published by the Chemical Rubber Publishing Co. 2310 Superior Are. N.E. Cleveland, Ohio, USA.*

Lyle J. Arnold Jr., et al. Assay Formats Involving Acridinium–Ester–Labeled DNA Probes, Clinical Chemistry, vol. 35, No. 8, 1989.

Sherrol H. McDonough et al. Application of Transcription–Mediated Amplification to Detection of Nucleic Acids From Clinically Relevant Organisms, p 113–123.

* cited by examiner

*Primary Examiner*—Ethan Whisenant
*Assistant Examiner*—Frank W Lu
(74) *Attorney, Agent, or Firm*—Oliff & Berridge, PL.C (57) ABSTRACT

The invention concerns a lysis method for a biological sample comprising at least one micro-organism of the bacteria type, for releasing a nucleic material of interest belonging to said micro-organism, which consists in: providing in a container a biological sample in liquid medium; providing in said container at least one particulate material, relatively hard, and substantially inert with respect to the nucleic material; submitting the biological sample and particulate material mixture to a movement. The invention is characterised in that in combination, the selected movement is of the vortex type, and satisfies the following conditions: the particulate material consists of beads with diameter between 90 and 150 $\mu m$; and the apparent volume of the beads (Vb) and the volume of the liquid sample (Ve) are linked by the relationship $Ve = \alpha \cdot Vb$, with $\alpha$ ranging between 1.4 and 10 when the container is tubular in shape, and $\alpha$ is not more than 2.1 when the container is in the shape of a disk; under such conditions, without any addition of reagent and/or additional process, the method consists in releasing directly into the liquid medium the nucleic material in native state and accessible to any reagent in a subsequent process.

20 Claims, 7 Drawing Sheets

Different combinations of beads/assay

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Staphylococcus epidermidis capture probe

<400> SEQUENCE: 1
gaccacctgt cactctgtcc c                                        21

<210> SEQ ID NO 2
<211> LENGTH: 21
<212> TYPE: DNA
<213> ORGANISM: Artificial Sequence
<220> FEATURE:
<223> OTHER INFORMATION: Staphylococcus epidermidis detection probe

<400> SEQUENCE: 2
ggaaggggaa aactctatct c                                        21

<210> SEQ ID NO 3
<211> LENGTH: 19
<212> TYPE: DNA
<213> ORGANISM: Artificial Sequence
<220> FEATURE:
<223> OTHER INFORMATION: primer for Staphylococcus epidermidis DNA

<400> SEQUENCE: 3
atcttgacat cctctgacc                                           19

<210> SEQ ID NO 4
<211> LENGTH: 19
<212> TYPE: DNA
<213> ORGANISM: Artificial Sequence
<220> FEATURE:
<223> OTHER INFORMATION: primer for Staphylococcus epidermidis DNA

<400> SEQUENCE: 4
tcgacggcta gctccaaat                                           19

<210> SEQ ID NO 5
<211> LENGTH: 26
<212> TYPE: DNA
<213> ORGANISM: Artificial Sequence
<220> FEATURE:
<223> OTHER INFORMATION: primer for Staphylococcus epidermidis 16s RNA

<400> SEQUENCE: 5
ggtttgtcac cggcagtcaa cttaga                                   26

<210> SEQ ID NO 6
<211> LENGTH: 26
<212> TYPE: DNA
<213> ORGANISM: Artificial Sequence
<220> FEATURE:
<223> OTHER INFORMATION: primer for Staphylococcus epidermidis 16s RNA

<400> SEQUENCE: 6
tcgaagcaac gcgaagaacc ttacca                                   26

<210> SEQ ID NO 7
<211> LENGTH: 18

```
<212> TYPE: DNA
<213> ORGANISM: Artificial Sequence
<220> FEATURE:
<223> OTHER INFORMATION: Staphylococcus epidermidis capture probe for
      16s RNA amplicon

<400> SEQUENCE: 7
gatagagttt tcccttc                                                    18

<210> SEQ ID NO 8
<211> LENGTH: 18
<212> TYPE: DNA
<213> ORGANISM: Artificial Sequence
<220> FEATURE:
<223> OTHER INFORMATION: Staphylococcus epidermidis detection probe for
      16s RNA amplicon

<400> SEQUENCE: 8
gacatcctct gacccctc                                                   18
```

LYSIS METHOD FOR MICRO-ORGANISMS

The present invention relates to a method of lysing a microorganism which makes it possible, in general, to disrupt the latter, especially the membrane of one or more cells, in order to release at least one nucleic material of interest, for example deoxyribonucleic acid (DNA) and ribonucleic acid (RNA) to be treated subsequently, in particular to be analysed.

The document U.S. Pat. No. 5,643,767 discloses a method of lysis for separating the DNAs or RNAs of cells in a liquid solution. A container is used for this purpose which contains a solvent for extracting the RNA or DNA, and a plurality of particles having a diameter of 0.1 to 1 mm, and at least one larger particle having a diameter of 3 to 5 mm. A movement is applied to the container thus filled, namely a shaking movement. It is expressly indicated in this document that this movement is preferred to a rotating movement, as generated with a mixer or another homogenizer, because with a rotating movement the cells simply turn in the same direction, and do not effectively collide with each other and with the beads so as to be crushed between the beads.

The document U.S. Pat. No. 4,295,613 discloses an apparatus for disrupting bacteria, according to which the sample containing the cells is placed in a tube in contact with Line beads. The beads, having a diameter of the order of 70 to 110 $\mu$m, are introduced into the tube, with the sample to be treated and any required buffer solution, and then an oscillating movement is applied to the container or tube along a horizontal axis, in order to obtain the subcellular constituents in solution such as enzymes, proteins, carbohydrates and the like.

The document FR-A-1,576,299 discloses a method for disrupting plant and animal cells, according to which a particulate material is used whose particle size is from 0.05 to 1 mm in diameter, it being possible for the particles to be made of steel or another similar material. A movement is applied to the mixture of biological sample and particles, according to a laminar flow.

The document EP-A-0,317,803 discloses a method for generating multilamellar liposomes encapsulating an aqueous medium. The method consists in mixing lipids and the aqueous medium to be encapsulated, in stirring the mixture in a container in the presence of particles having a diameter of less than 3 mm, the preferred size being 50 to 100 $\mu$m, in order to obtain liposomes having a diameter of about 150 to 3000 nanometers.

The document EP-A-0,796,917 discloses a device which releases particles into a biological sample containing cells. When the sample is stirred or sonicated, this device comprises a partition which retains the particles during a sufficient period, and then releases them and disrupts the cells, which thus makes it possible to make the nucleic acids accessible. The particles retained by the partition, which are made of glass, plastic or a metal such as zirconium, may have different shapes, and have a diameter of about 0.1 to 0.15 mm. One particle is assigned to breaking the partition, and has a diameter of about 1 to 4 mm, preferably 3 mm. The apparatus for subjecting to an alternating movement is a stirrer of the Biospec® trade mark.

The document EP-A-0,288,618 discloses a method of cell lysis, including microorganisms, in order to release subcellular constituents including DNA and RNA into solution. The biological sample is placed in a container with particles of different sizes. The container is then subjected to sonication until the cells release their constituents. The ultrasound causes the particles to vibrate through the sample, which causes the disruption of the cells by shearing. The particles are glass beads having a diameter of between 0.05 and 1 mm. The sonication time is 10 minutes at room temperature. The RNA and DNA are released in a manner accessible to genetic nucleic hybridization probes.

The document U.S. Pat. No. 5,464,773 discloses an apparatus for lysing cells, without destroying the subcellular constituents, in order in particular to release the RNA and DNA so as to subsequently carry out a hybridization. The container used contains two sizes of beads made of zirconium, glass or plastic and the like. In a preferred mode, the container contains 400 $\mu$l of particles of zirconium of two different sizes and weights, for example 0.7 g and 0.1 mm in diameter and 0.65 g and 0.5 mm in diameter. The movement applied to the container is a vibratory-type, in particular oscillatory-type, movement.

The document U.S. Pat. No. 4,666,850 discloses an apparatus and a method for lysing a blood sample during its centrifugation. The container receiving the blood sample contains particles or beads, made of plastic or glass, which should have a size which does not prevent the sedimentation of bacteria at the bottom of the tube during centrifugation.

The document EP-A-0,341,215 discloses a method for producing heterologous proteins from genetically transformed yeasts. To evaluate the quantity of proteins, it is simply specified that to lyse the cells, mechanical shearing forces are applied by shaking the biological sample containing the yeasts with glass beads.

The document EP-A-0,284,044 discloses a method for increasing the production of proteins in yeasts. It is indicated that the cells (yeasts), for analysing the quantity of proteins, are preferably lysed by applying a vortex-type movement to the biological sample, with glass beads having a diameter of 450–500 $\mu$m at a maximum speed for one minute, three times in succession.

The document U.S. Pat. No. 4,775,622 discloses a method for expressing and recovering proteins from a yeast culture.

The methods generally used for lysing a biological sample comprising at least one microorganism, specifically for releasing at least one nucleic material of interest, essentially consist according to the prior art in that:
  a biological sample in a liquid medium, comprising the microorganism to be lysed, is placed in a container,
  at least one particulate material which is relatively hard and substantially inert relative to the nucleic material is placed in said container,
  and the mixture of biological sample and particulate material is essentially subjected to an alternating movement, of variable amplitude and/or frequency if it is a regular movement, depending on the technique or the equipment chosen for causing the movement.

These methods which are used have some disadvantages. They are not sufficiently effective, in particular the cell lysis proves to be inadequate in quantity and quality for releasing the nucleic material.

Furthermore, they do not always make it possible to lyse cells which are reputed to be resistant to lysis, in particular the cells of Gram+bacteria, for example those of Mycobacteria.

Likewise, the use of these methods often requires the addition of additional reagents such as, for example, enzymes and/or detergents.

According to the present invention, it is found that, contrary to the teaching disclosed in U.S. Pat. No. 5,643, 767, a rotating movement of the vortex type was particularly suitable for lysing microorganisms and releasing the nucleic material of interest directly, provided that certain parameters for this movement are chosen, in relation in particular to the container.

The subject of the invention is therefore a method of complete, effective and simple lysing of a biological sample comprising at least one microorganism, with no reagent and/or additional operating step during the use of the method.

The first subject of the present invention is therefore a method of lysing a biological sample comprising at least one microorganism of the bacterium type, in order to release at least one nucleic material of interest belonging to said microorganism, according to which:

said biological sample in a liquid medium is placed in a container,
at least one particulate material which is relatively hard and substantially inert relative to the nucleic material is placed in said container,
the mixture of biological sample and particulate material is subjected to a movement,
characterized in that, in combination:
the movement chosen is of the vortex type, and corresponds to the following conditions:
the particulate material consists of beads having a diameter of between 90 and 150 $\mu$m, and
the apparent volume of the beads, Vb, and the volume of the liquid sample, Ve, are linked by the relationship Ve=$\alpha$.Vb, with a between 1.4 and 10 when the container is in tubular form, and $\alpha$ less than or equal to 2.1 when the container is in disk form,
whereby, without addition of reagent and/or additional operating step, the nucleic material is released directly into the liquid medium in the native state and in a state accessible to any reagent.

A second subject of the invention is a method of lysing a biological sample comprising at least one microorganism of the yeast type, in order to release at least one nucleic material of interest belonging to said microorganism, according to which:

said biological sample in a liquid medium is placed in a container,
at least one particulate material which is relatively hard and substantially inert relative to the nucleic material is placed in said container,
the mixture of biological sample and particulate material is subjected to a movement, characterized in that, in combination:
the movement chosen is of the vortex type, and corresponds to the following conditions:
the particulate material consists of beads having a diameter of about 500 $\mu$m, and
the apparent volume of the beads, Vb, and the volume of the liquid sample, Ve, are linked by the relationship Ve=$\alpha$.Vb, with a between 1.4 and 10 when the container is in tubular form, and $\alpha$ less than or equal to 2.1 when the container is in disk form,
whereby, without addition of reagent and/or additional operating step, the nucleic material is released into the liquid medium in the native state and in a state accessible to any reagent.

Using the method according to the invention, the nucleic material is obtained in the native state, which means that it is essentially not degraded, for example not denatured, or that it conserves practically all the characteristics or properties which it had inside the cell or organism from which it is extracted.

Moreover, the method according to the invention is sufficiently effective to allow the lysis of a single microorganism, which is of particular importance for many methods of biological analysis, especially for the techniques of amplification or analysis by hybridization of nucleic probe(s).

As regards the nucleic material, the present invention offers the decisive advantage of releasing said material in a manner directly accessible for any subsequent protocol relating to it, for example one or more amplification primers, one or more hybridization probes and the like.

Consequently, according to the present invention, the lysed biological sample obtained may be treated directly, that is to say with no intermediate operating step, or with no added reagent, according to any operating protocol in relation with the nucleic material of interest released, such as amplification, analysis, and the like, with any appropriate nucleic reagents, and the like.

In a preferred embodiment according to the first subject of the invention, the particulate material consists of beads having a diameter of about 100 $\mu$m, for a microorganism of the bacterium type.

In another embodiment according to the first or second subject of the invention, the vortex-type movement satisfies, in addition, the following relationship:
Vb<Ve<Vc, according to which
Vc=$\beta$.Ve, and
$\beta$ is greater than or equal to 2.5, Vc being the useful volume of the container.

The containers which may be used according to the invention may be of different formats, for example in tubular form or in disk form.

It is preferable that the container is in tubular form, preferably with a U-shaped bottom. In this preferred embodiment, $\beta$ is a number between 2.5 and 30.

In yet another embodiment according to the invention, the containers are in disk form and in tubular form with a U-shaped bottom (such as for example of the Falcons® type) or with a frustoconical 30 bottom (such as for example of the Eppendorf® type).

When the container is in disk form, $\alpha$ is a number less than or equal to 2.1, preferably less than or equal to 1.4 and $\beta$ is a number greater than or equal to 9.3.

It is preferable that the container is a tube with a frustoconical bottom such as an Eppendorf tube, $\alpha$ being between 1.4 and 10, preferably between 1.4 and 3.3, and $\beta$ being between 2.5 and 30, preferably between 2.5 and 15, still more preferably between 3.75 and 15.

It is also preferable that the container is a tube with a U-shaped bottom, such as a Falcon tube, $\alpha$ being between 1.4 and 10, preferably between 1.4 and 3.3, still preferably is equal to 3.3, and $\beta$ being between 3 and 30, preferably between 12 and 30, still preferably is equal to 20.

In yet another embodiment according to the invention, the particulate material comprises other beads having a diameter greater than that of said beads. It is preferable that the container comprises up to 16, preferably 10 other beads. It is even more preferable that these other beads have a diameter of about 2 to 3 mm.

This additional characteristic of the method according to the invention makes it possible, for an equivalent efficiency, in particular to reduce or limit the time required for the lysis of the biological sample.

This additional characteristic also makes it possible to disrupt complex biological samples, such as living tissues, before the actual lysis itself.

In yet another embodiment according to the invention, an antifoaming substance may be added to the biological sample to a final concentration of 0.01 to 1% by volume, preferably of 0.5 to 1% by volume of the liquid sample, Ve.

It is also possible, according to another embodiment, to add a detergent of the anionic type to the biological sample to a final concentration of 2.5% of the volume of the liquid sample, Ve.

In a preferred embodiment according to the first subject of the invention, the time for putting through a vortex-type movement is at least equal to 10 seconds, preferably at least equal to 20 seconds, advantageously between 1 and 5 minutes.

The vortexing time is adjusted so as to obtain a percentage lysis at least greater than or equal to 20%.

It is also preferable, according to the specificities of the lysis protocol used, especially when beads having a larger diameter are added, that the time for putting through a vortex-type movement is about 2 minutes.

In a preferred embodiment according to the second subject of the invention, the time for putting through a vortex-type movement is between 8 and 20 minutes.

Given that the lysate obtained directly makes it possible to detect and/or quantify and/or amplify the nucleic material of interest, the present invention also relates to a method of treating a biological sample comprising one microorganism comprising a nucleic material of interest, said method comprising:

a) a lysis step, according to which:
    said biological sample in a liquid medium is placed in a container,
    at least one particulate material which is relatively hard and substantially inert relative to the nucleic material is placed in said container,
    and the mixture of biological sample and particulate material is subjected to a vortex-type movement, according to which in combination:
        the beads have a diameter of between 90 and 150 $\mu$m for a microorganism of the bacterium type, and of about 500 $\mu$m for a microorganism of the yeast type,
        the apparent volume of the beads, Vb, and the volume of the liquid sample, Ve, are linked by the relationship Ve=$\alpha$.Vb, with $\alpha$ between 1.4 and 10 when the container is in tubular form, and $\alpha$ less than or equal to 2.1 when the container is in disk form, b) the lysed biological sample, with or without the particulate material which served for the lysis, is subjected directly to an operating protocol relating specifically to the nucleic material of interest, for example nucleic amplification and/or detection and/or quantification.

Thus, for example after amplification, at least $1\times10^2$ cells/ml can be detected.

A third subject according to the invention is a container for a single use, for carrying out the method described above, characterized in that it comprises a load of a particulate material suited, depending on a predetermined volume of the biological sample, to the direct carrying out of the method described above.

"Biological sample" is understood to mean any sample, specimen or fraction of a biological material, which may be simple or complex, for example a living tissue or a body liquid or fluid. This biological sample contains at least one microorganism to be lysed, with or without prior treatment of the structure comprising said microorganism, for example destruction of the organization of the tissue.

"Microorganism" is understood to mean any biological material, naturally comprising a closed membrane or envelope, one or more subcellular biological constituents of interest enclosed inside said membrane or envelope, namely nucleic constituents (DNA or RNA). By way of example, there may of course be mentioned prokaryotic microorganisms such as bacteria and archaebacteria, eukaryotic microorganisms such as plant or animal cells, yeasts and fungi, also various living tissues, and by extension viral particles.

The term "lysis" is understood to mean any process which makes it possible to disrupt the abovementioned membrane or envelope in order to release the nucleic material of interest, in a complete or partial form.

The following figures and examples make it possible to illustrate the subject of the invention but do not limit the scope thereof in any way.

"SI" means "initial solution" and represents the control which was not lysed.
    A: Glass beads of 1 to 50 $\mu$m
    B: Glass beads of 50 to 100 $\mu$m
    C: Glass beads of 90 to 150 $\mu$m
    D: Glass beads 100 $\mu$m
    E: Zirconium beads 100 $\mu$m
    F: Zirconium beads 500 $\mu$m
    G: 50/50 mixture of zirconium beads of 100 and 500 $\mu$m.

"SI" means "initial solution" and represents the control which was not lysed.
    A: Glass beads of 1 to 50 $\mu$m
    B: Glass beads of 50 to 100 $\mu$m
    C: Glass beads of 90 to 150 $\mu$m
    D: Glass beads 100 $\mu$m
    E: Zirconium beads 100 $\mu$m
    F: Zirconium beads 500 $\mu$m
    G: 50/50 mixture of zirconium beads of 100 and 500 $\mu$m.

FIG. 9 illustrates the percentage lysis (on the y-axis) as a function of the geometry of the container (on the x-axis).
    A: Eppendorf tube with a V-shaped bottom, Vc=1.5 ml
    B: flat-bottomed spectrophotometer cuvette, Vc=5 ml
    C: flat-bottomed tube, Vc=30 ml
    D: flat-bottomed tube, Vc=60 ml
    E: flat-bottomed glass bottle, Vc=8 ml
    F: flat-bottomed glass bottle, Vc=25 ml G: polystyrene tube with a U-shaped bottom, Vc=6 ml
H: polystyrene tube with a U-shaped bottom, Vc=14 ml
I: polystyrene tube with a U-shaped bottom, Vc=22 ml
J: polypropylene tube with a U-shaped bottom, Vc=6 ml
K: polypropylene tube with a U-shaped bottom, Vc=14 ml
L: polypropylene tube with a U-shaped bottom, Vc=22 ml
M: polypropylene tube with a U-shaped bottom, Vc=4 ml.

A: 10 stainless steel beads of diameter 2 mm
B: 10 glass beads of diameter 3 mm
C: 5 stainless steel beads and 5 glass beads of diameters 2 and 3 mm respectively
D: 4 stainless steel beads and 4 glass beads of diameters 2 and 3 mm respectively
E: 5 stainless steel beads and 3 glass beads of diameters 2 and 3 mm respectively
F: 3 stainless steel beads and 5 glass beads of diameters 2 and 3 mm respectively.

In order to determine the efficiency of the method of lysis according to the invention, a general test protocol was developed for analyzing the lysate obtained by measuring the percentage lysis.

This general protocol is described below.

Bacteria with Gram+ wall, *Staphylococcus epidernidis* (bioMérieux reference API No. 8149310), cultured in BHB (Brain Heart Broth) liquid medium are centrifuged at 2500 revolutions/minute for 10 minutes at 25° C. before being resuspended either in BHB medium or in lysis buffer at the concentration of $5 \times 10^9$ cells/300 µl. The composition of the lysis buffer is the following: 30 mM Tris-HCl, 5 mM EDTA, 100 mM NaCl, pH 7.2. 300 µl of the suspension are added to a tube containing beforehand a defined volume of glass beads. The closed tube is subjected to a vortex-type movement for 2 minutes, at the maximum power of the apparatus (Reax 2000, Heidolph). The bacterial suspension thus treated is stored on ice before analysis.

The percentage lysis is determined immediately after collecting the sample, by measuring the optical density at 550 nm. The percentage lysis is equal to the ratio of the OD value at 550 nm of the bacterial solution after vortexing to the OD value at 550 nm before vortexing.

The quality of the nucleic acids released by the vortexing step is verified on a 0.8% agarose gel. 10 µl of the lysate are deposited per well, the migration is carried out at constant voltage (150 V) and the gel is stained with ethidium bromide (EtBr) before observation under ultraviolet radiation.

The quantity of nucleic acids released by the vortexing step is determined by specific detection according to the so-called sandwich hybridization technique using the Vidas® apparatus marketed by bioMérieux (France). Capture and detection oligonucleotide probes specific for the nucleic acids of *S. epidermidis* (see patent EP 0,632,269) were chosen. The capture and detection oligonucleotides have the sequence: 5'-GACCACCTGTCACTCTGTCCC-3' (SEQ ID No.:1) and 5'-GGAAGGGGAAAACTCTATCTC-3' (SEQ ID No.:2), respectively. The detection probe is labeled by coupling with alkaline phosphatage (AP). The specific hybridization of these probes with the nucleic acids released into the lysate depends on the quantity of nucleic acids present, but also on their accessibility for the probes used.

Two amplification protocols specific for the DNA and RNA molecules of *S. epidermidis* were carried out starting with lysates collected in order to verify if the nucleic acids released by vortexing can be amplified: a PCR protocol for the amplification of the DNA and an NASBA protocol for the amplification of the 16S rRNA.

PCR protocol: the PCR technique followed is that described by Goodman in PCR stratégies, Ed: Innis, Gelford and Snisky Académie press 1995, pp 17–31. Two amplification primers were used; they have the following sequences Primer 1: 5'-ATCTTGACATCCTCTGACC-3' SEQ ID No.:3

Primer 2: 5'-TCGACGGCTAGCTCCAAAT-3' SEQ ID No.:4

The following temperature cycles were used

| Once | 3 minutes | 94° C. |
| | 2 minutes | 65° C. |
| 35 times | 1 minute | 72° C. |
| | 1 minute | 94° C. |
| | 2 minutes | 65° C. |
| Once | 5 minutes | 72° C. |

NASBA protocol: the NASBA technique followed is that described by Van der Vliet et al., J. Gen. Microbiol. 1993, 139: 2423. Two amplification primers were used; they have the following sequences:

Primer 1: 5'-GGTTTGTCACCGGCAGTCAACTTAGA-3' (SEQ ID No.: 5)

Primer 2: 5'-TCGAAGCAACGCGAAGAACCTTACCA-3' (SEQ ID No.: 6)

10 µl of lysate or 5 µl of lysate are used for each PCR and NASBA assay, respectively. The amplicons produced by PCR are observed on 0.8% agarose gel and quantified on a Vidas apparatus according to the protocol described above. The amplicons produced after NASBA are detected and quantified on microplate by hybridization with a capture probe and a detection probe specific for *S. epidermidis*, according to the method described by P. Cros et al., Lancet 1992, 240: 870. The detection probe is coupled with horseradish peroxidase (HRP). The two probes have the following sequences:

Capture probe: 5'-GATAGAGTTTTCCCCTTC-3' (SEQ ID No.: 7)

Detection probe: 5'-GACATCCTCTGACCCCTC-3' (SEQ ID No.: 8)

Example 1

Influence of the Diameter of the Beads and of the Coefficient a on the Efficiency of the Vortex Lysis a—Influence of the Diameter of the Beads The lysis protocol was carried out as described above starting with an initial suspension of *Staphyloccus epidermidis* ($5 \times 10^9$ cells/300 µl) in the presence of 90 µl of different mixtures of beads characterized by different diameters, for 2 minutes per experiment. The diameters tested are between 1 and 500 µm; the mixtures tested are the following:

A: glass microbeads having a diameter of between 1 and 500 µm,

B: glass microbeads having a diameter of between 50 and 100 µm,

C: glass microbeads having a diameter of between 90 and 150 µm,

D: homogeneous mixture of beads of diameter 100 µm,

E: homogeneous mixture of zirconium beads of diameter 100 µm

F: homogeneous mixture of zirconium beads of diameter 500 µm

G: mixture (50/50 v/v) of zirconium beads of diameter 100 and 500 µm.

Figure 1:
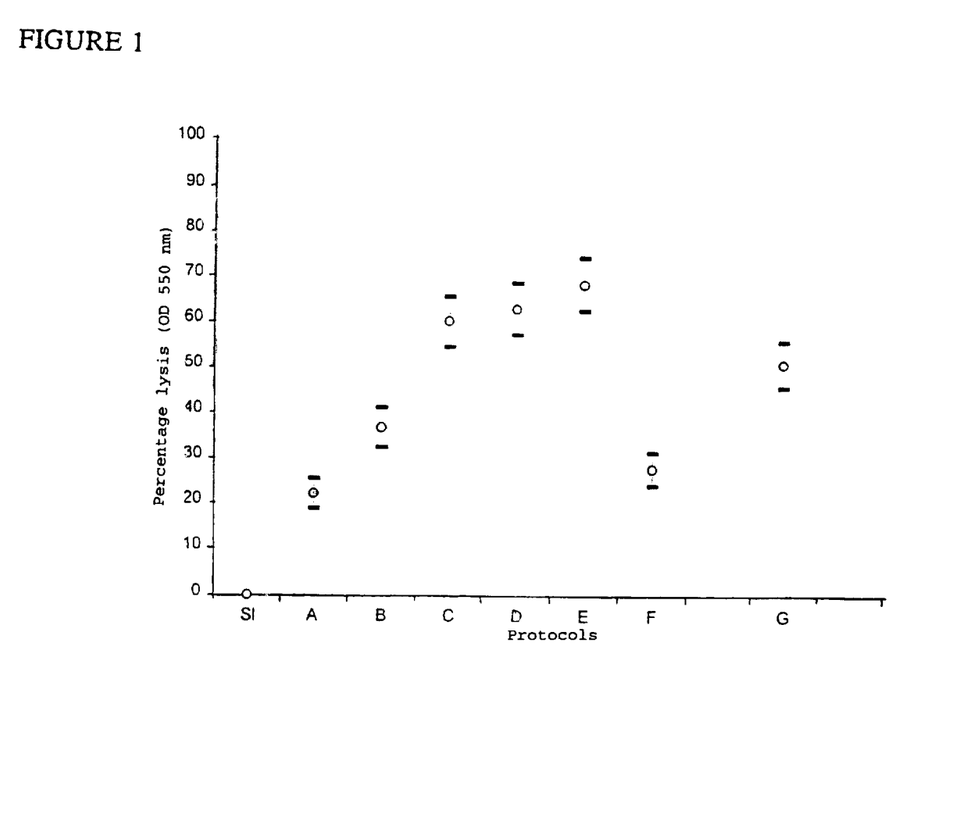
FIG. 1 illustrates the percentage lysis (on the y-axis) as a function of the diameter of the beads (on the x-axis), and of the composition of the mixture (nature and proportion of the beads).
Figure 2:
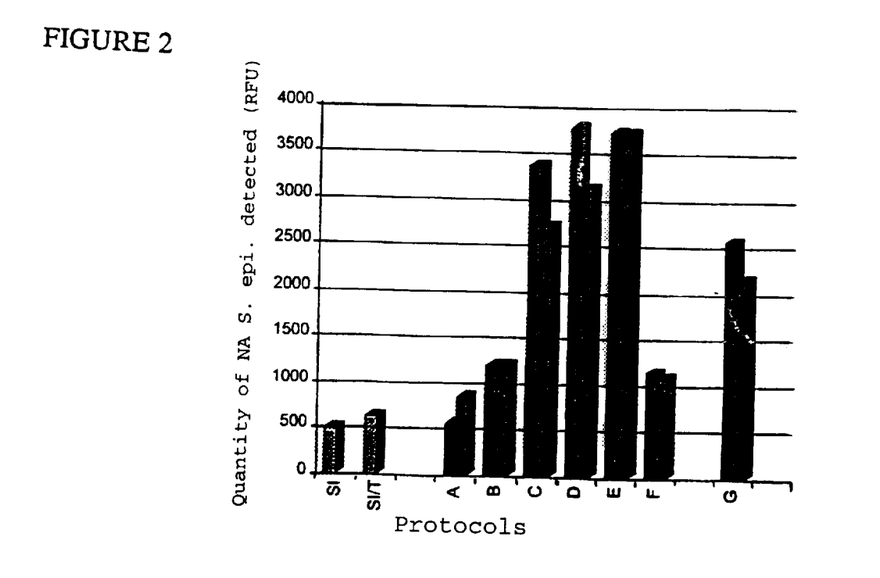
FIG. 2 illustrates the quantity of nucleic acids of *S. epidermidis* detected (on the y-axis) as a function of the diameter of the beads (on the x-axis).

As indicated in FIG. 1, the cell lysis obtained is the most effective in the presence of beads having a diameter of between 90 and 150 µm, and preferably equal to 100 µm. The measurements of optical density at 550 nm of the samples collected after vortexing for 2 minutes under these conditions indicate that the percentage lysis of *S. epidermidis* is between 60 and 70% with this bead diameter. Only negligible differences in the percentage lysis are observed according to the nature of the beads (glass or zirconium) of the same diameter. On the other hand, the use of beads having a diameter of less than or greater than 90 up to 150 µm, such as the mixtures of beads of diameter 1 to 50 µm, 50 to 100 µm, 100 to 500 µm, or the homogeneous mixture of beads of diameter 500 µm causes a reduction in the percentage lysis. Analysis on 0.8% agarose gel of the nucleic acids released into the lysates, presented in FIG. 2, shows that the DNA and rRNA molecules are well conserved since their migration profile on 0.8% agarose gel is the same as that of the molecules of purified and commercially available bacterial DNA and rRNA. The nucleic acids released also have the same migration profile regardless of the diameter of the beads used for the cell lysis. The nucleic acids released can also be detected by Vidas analysis of which the protocol is described above. Still according to FIG. 2, the quantity of nucleic acids released into the lysates, measured by Vidas analysis, reflects the percentage lysis obtained. In parallel, it was demonstrated that the DNA or 16S rRNA of each lysate can be amplified by PCR or NASBA protocol specific for *S. epidermidis*, which are described in the general test protocol section above.

b—Influence of the Coefficient α

Eppendorf Tube

The lysis protocol was carried out in the presence of beads having a diameter of 100 µm, for 2 minutes. Identical Eppendorf tubes were used for all the experiments. The volume of the bacterial suspension was set at 300 µl/tube for each experiment, and the volume of beads varied between 1 and 300 µl/tube. That is Vb, the apparent volume of the beads and Ve, the volume of the liquid sample such that Vb<Ve with Ve=α.Vb with α being a positive real number different from 0. The coefficient α varied from 1 to 300. After the vortexing step, the samples collected are analyzed by measuring the optical density at 550 nm, the nucleic acids released into the lysate are examined on 0.8% agarose gel and quantified by Vidas analysis.

Figure 3:
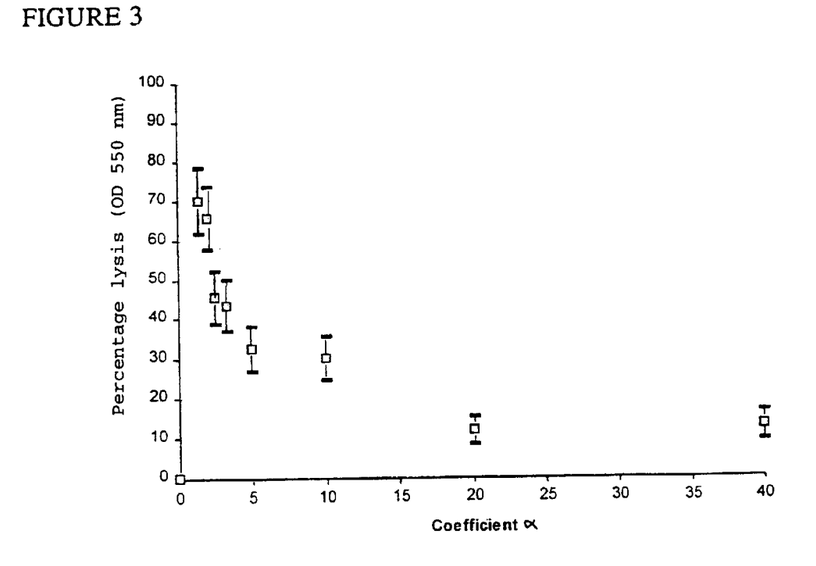
FIG. 3 illustrates the percentage lysis (on the y-axis) in an Eppendorf tube as a function of the coefficient a (on the x-axis).

FIG. 3 indicates that the lysis of *S. epidermidis* is effective for a coefficient values of between 1.4 and 10: the percentage lysis is between 30 and 70%. For values of α<1.4, the volume of beads being too high, the dead volume of the cellular suspension increases to such an extent that it is impossible to recover the initial volume of the cellular suspension. For values of α>10, the volume of beads is low and the probability of meeting and of mechanical shock between beads and cells is reduced. Preferably, the cell lysis is more effective for α values of between 1.4 and 3.3: the percentage lysis being between 40 and 70%. Analysis on 0.8% agarose gel of the lysate shows that the migration profiles of the nucleic acids released are not modified, regardless of the values of α. The quantity of nucleic acids measured by Vidas analysis is directly correlated with the percentage lysis.

Falcon Tube

Figure 4:
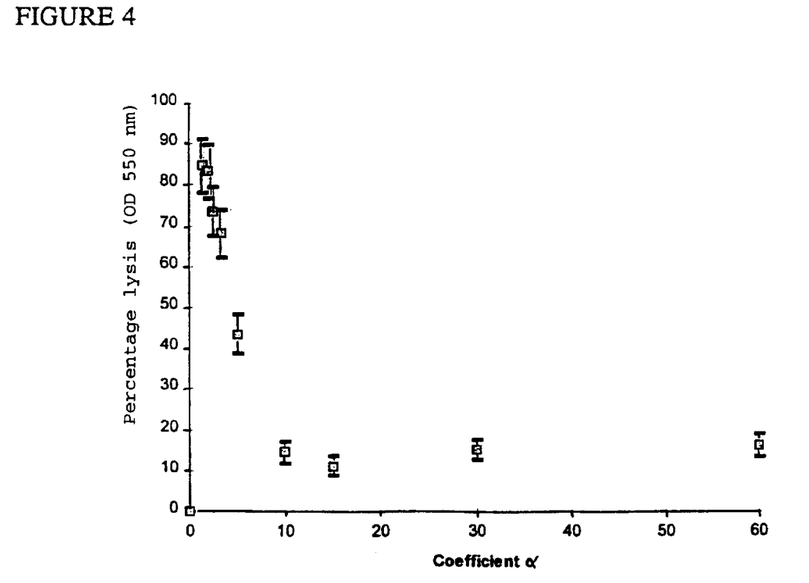
FIG. 4 illustrates the percentage lysis (on the y-axis) in a Falcon tube as a function of the coefficient a (on the x-axis).

The same study was carried out, replacing the Eppendorf tubes with Falcon tubes made of polypropylene (Vc=6 ml). FIG. 4 indicates that the lysis of *S. epidermidis* is effective for a coefficient values of between 1.4 and 10: the percentage lysis is greater than 20%. Preferably, the cell lysis is more effective for α values of between 1.4 and 3.3: the percentage lysis is between 65 and 85%.

Disk Form

A card having the dimensions l=L=8.5 cm and h=0.4 cm was used. One or more holes, defined as wells, are made which have a constant height equal to the height of the card (that is 0.4 cm) and which have a constant diameter. These wells are covered with a film on either side, and each well is filled with a mixture of beads having a diameter of 100 µl, an apparent volume Vb, of 10 iron beads having a diameter of 2 mm and of a cellular suspension of volume Ve. The card thus defined is maintained on the vortex.

The lysis protocol was carried out for two minutes. Cards as described above with a diameter of 30 cm (Vc=2.8 ml/well) were used for each experiment. The volume of the bacterial suspension was set at 700 µl/well and the volume of beads varied from 90 to 510 µl/well. The coefficient α varied from 1.4 to 7.8. After the vortexing step, the percentage lysis of the samples collected was analyzed by measuring the optical density at 550 nm, the nucleic acids released were examined on agarose gel and quantified by Vidas analysis.

Figure 5:
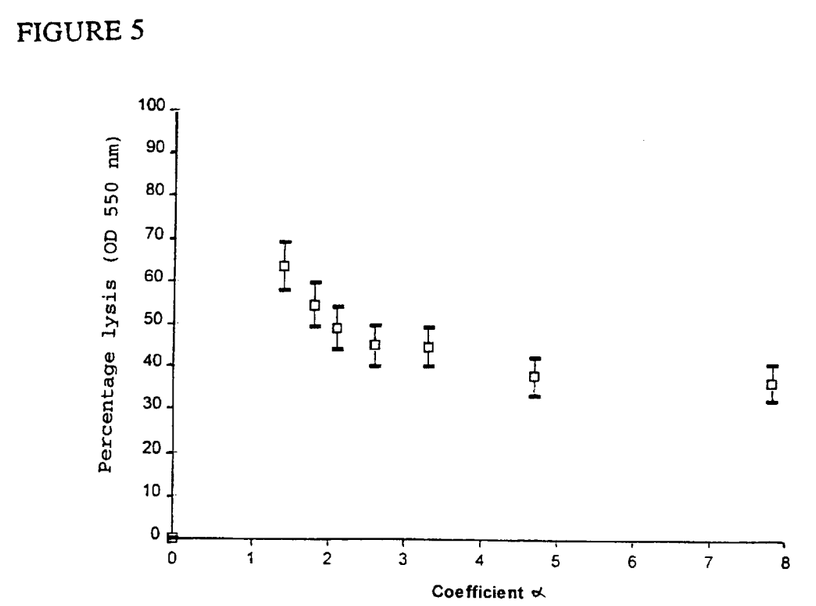
FIG. 5 illustrates the percentage lysis (on the y-axis) in a container in disk form as a function of the coefficient a (on the x-axis).

FIG. 5 indicates the percentage lysis obtained as a function of the coefficient α. The lysis of *S. epidermidis* is effective with a container having a "card" format for coefficient values of less than or equal to 2.1: when α is between 1.4 and 2.1, the percentage lysis is between 45% and 75%. Preferably, the optimum value of the coefficient ought to be less than 1.4 because even for α values approaching 1.4, the percentage lysis values do not arrive at a plateau. Analysis on 0.8% agarose gel of the lysate shows that the released nucleic migration profiles are not modified regardless of the values of α. The quantity of nucleic acid measured by Vidas analysis is directly correlated with the percentage lysis.

Example 2

Influence of the Coefficient β on the Efficiency of the Vortex Lysis

Eppendorf Tube

The lysis protocol was carried out in the presence of a constant ratio between the apparent volume of beads and the volume of the liquid sample (α=Ve/Vb=3.3) for 2 minutes. The volume of the bacterial suspension varied between 100 µl and 1 ml. That is Ve, the volume of liquid sample and Vc, the useful or available volume of the container such that Ve<Vc and Vc=β.Ve with β being a positive real number greater than 0, the coefficient β varied from 1.5 to 15. The experiments were carried out in an Eppendorf tube, that is Vc=1.5 ml. After the vortexing step, the samples collected are analyzed by measuring the optical density at 550 nm, the nucleic acids in the lysate are examined on 0.8% agarose gel and analyzed by Vidas analysis.

Figure 6:
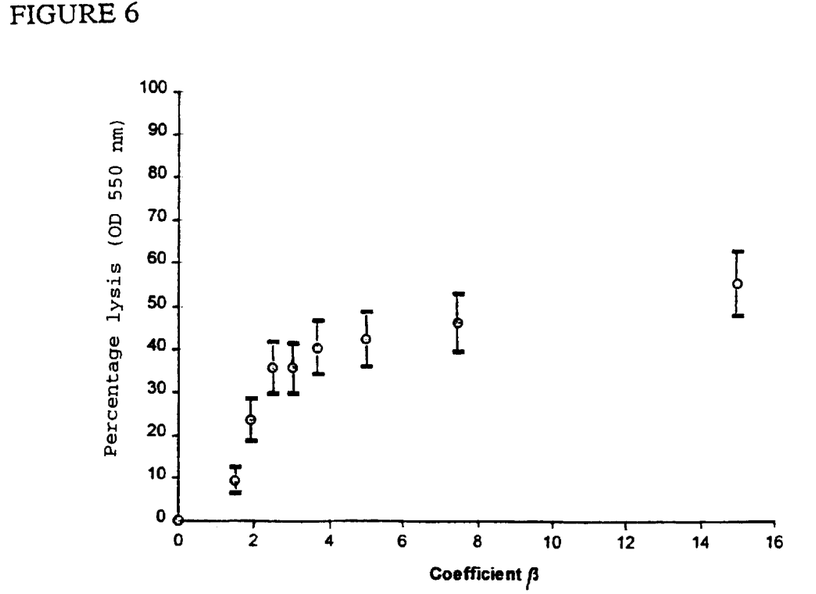
FIG. 6 illustrates the percentage lysis (on the y-axis) in an Eppendorf tube as a function of the coefficient b (on the x-axis).

The percentage lysis obtained as a function of the coefficient β is indicated in FIG. 6. The lysis of *S. epidermidis* is more effective for β coefficient values of between 2.5 and 15: the percentage lysis is greater than 30%. For values of β less than 2.5, the volumes of beads and of liquid sample are too high; they limit the movement of the beads in the sample and the dead volume of the sample increases. For values of β greater than 15, the volume of the sample is too low to allow complete recovery of the initial volume of the cellular suspension for α=3.3. Preferably, the efficiency of cell lysis is better for β values of between 3.75 and 15: the percentage lysis is between 35 and 60%; preferably for values of between 7.5 and 15 (40 to 60% lysis). Analysis on 0.8% agarose gel of the lysates shows that the migration profiles of the nucleic acids released are the same regardless of the values of β. The quantities of nucleic acids measured by Vidas analysis are directly correlated with the percentage lysis obtained.

Falcon Tube

Figure 7:
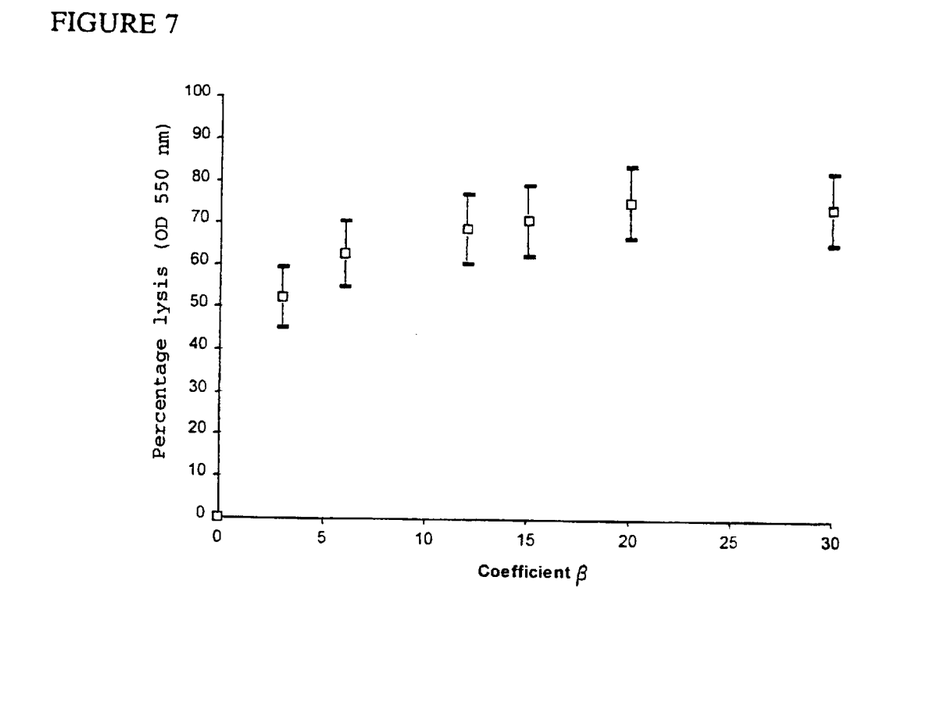
FIG. 7 illustrates the percentage lysis (on the y-axis) in a Falcon tube as a function of the coefficient b (on the x-axis).

A similar study was carried out using polypropylene Falcon tubes (Vc=6 ml) in place of the Eppendorf tubes. The same value of the coefficient α was set (α=3.3). The volume of the bacterial suspension varied between 200 μl and 2 ml. β varied from 3 to 30. FIG. 7 illustrates the percentage lysis obtained as a function of the coefficient β. The lysis of *S. epidermidis* is more effective for β values of between 6 and 30: the percentage lysis is greater than 50%. For values of β>30, the volume of the sample is too low to allow complete recovery of the initial volume of the cellular suspension, for α=3.3. Preferably, the efficiency of the cell lysis is better for β values of between 12 and 30: the percentage lysis is greater than 60%.

Disk Form

The lysis protocol was carried out with the same container used in Example 1 (diameter of the wells 30 mm, Vc=2.8 ml), with a value of coefficient α (α=3.3) for two minutes. The volume of the bacterial suspension varied from 300 to 700 μl/well. The coefficient β varied from 4 to 9.3. After the vortexing step, the percentage lysis of the samples recovered was analyzed by measuring the optical density at 550 nm. The nucleic acids released were examined on agarose gel and quantified by Vidas analysis.

Figure 8:
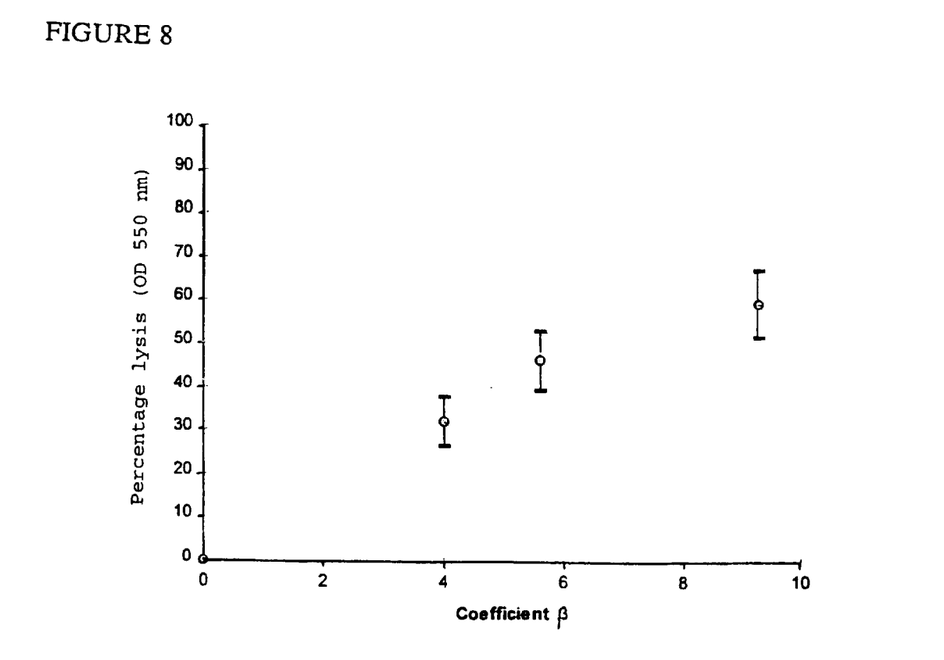
FIG. 8 illustrates the percentage lysis (on the y-axis) in a container in disk form as a function of the coefficient b (on the x-axis).

The percentage lysis obtained as a function of the coefficient β is indicated in FIG. 8. The lysis of *S. epidermidis* is effective in a container having a "card format" for β values greater than or equal to 9.3. When β is equal to 9.3 with a non-optimum value of a (α=3.3), 60% of the cells are lysed. Analysis on 0.8% agarose gel of the lysate shows that the migration profiles of the nucleic acids released are not modified regardless of the values of β and are similar to those described for the tube format. The quantity of nucleic acids measured by Vidas analysis is correlated with the percentage lysis for each experiment.

Example 3

Influence of the Geometry of the Tube on the Efficiency of the Vortex Lysis

The lysis protocol was carried out in containers with different geometries and different volumes (Vc), in the presence of 300 μl of cellular suspension and 90 μl of beads having a diameter of 100 μm for 2 minutes (that is α=3.3 and β variable).

A: polypropylene Eppendorf tube with a V-shaped bottom, Vc=1.5 ml

B: flat-bottomed polypropylene spectrometer cuvette, Vc=5 ml

C: flat-bottomed tube, Vc=30 ml

D: flat-bottomed tube, Vc=60 ml

E=flat-bottomed glass bottle, Vc=8 ml

F=flat-bottomed glass bottle, Vc=25 ml

G=polystyrene tube with a U-shaped bottom, Vc=6 ml

H=polystyrene tube with a U-shaped bottom, Vc=14 ml

I=polystyrene tube with a U-shaped bottom, Vc=22 ml

J=polypropylene tube with a U-shaped bottom, Vc=6 ml

K=polypropylene tube with a U-shaped bottom, Vc=14 ml

L=polypropylene tube with a U-shaped bottom, Vc=22 ml

M=polypropylene tube with a U-shaped bottom, Vc=4 ml.

Figure 9:
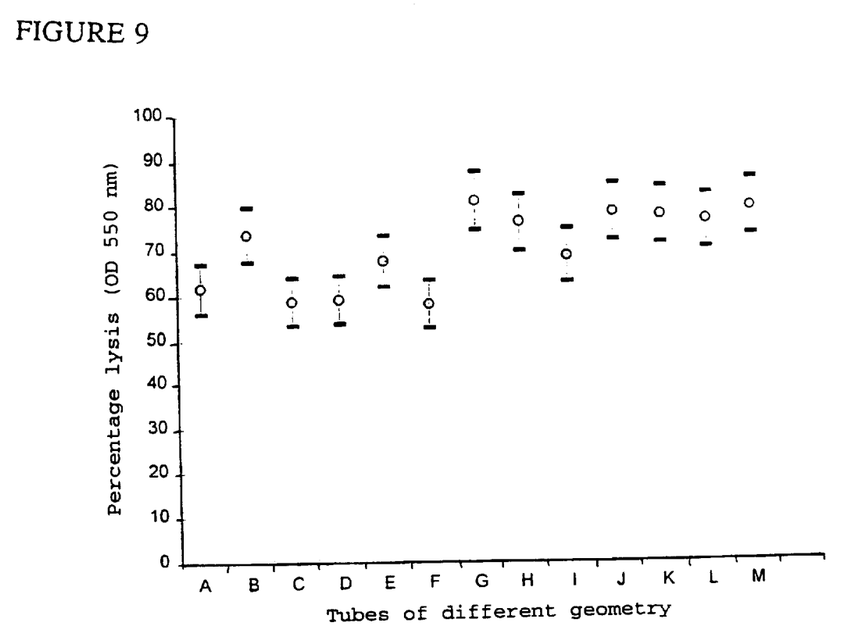

FIG. 9 shows the percentage lysis obtained as a function of the geometry of the container used. The percentage lysis is on average between 60 and 75% with the tubes with a flat bottom and with a V-shaped bottom, on the other hand it is on average between 70 and 80% with the tubes with a U-shaped bottom for the same vortexing time and the same value of α. Measurement, by Vidas analysis, of the quantity of nucleic acids released confirms this influence.

Example 4

Influence of the addition of Beads With a Larger Diameter on the Efficiency of the Vortex Lysis The lysis protocol was carried out in an Eppendorf tube, in the presence of 300 μl of cellular suspension and 90 μl of beads having a diameter of 100 μm (that is α=3.3 and β=5) for two minutes. Various beads were added to the medium in combination: iron beads having a diameter of 2 mm, glass beads having a diameter of 3 mm.

Figure 10:
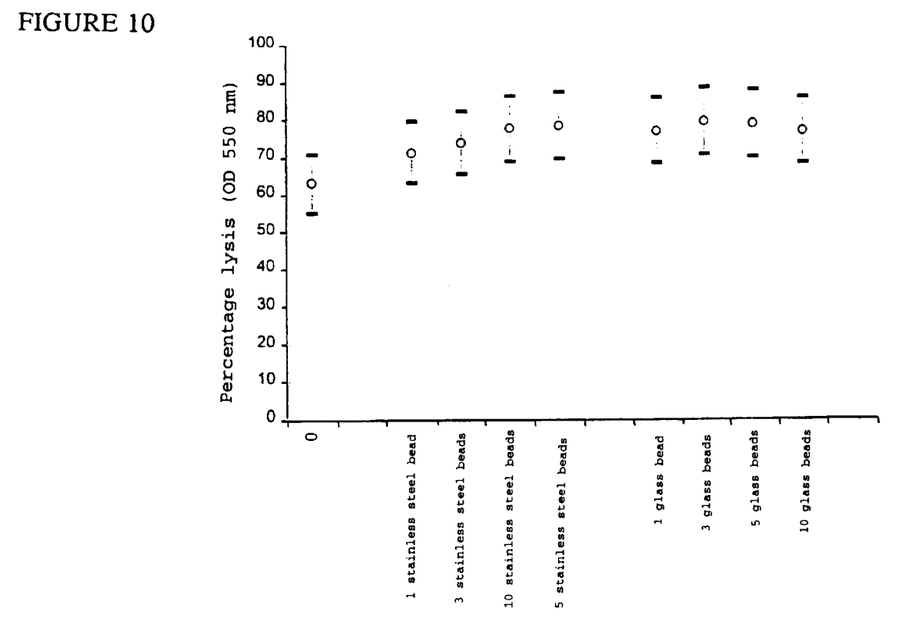
FIG. 10 illustrates the percentage lysis (on the y-axis) as a function of different beads added (on the x-axis).
Figure 11:
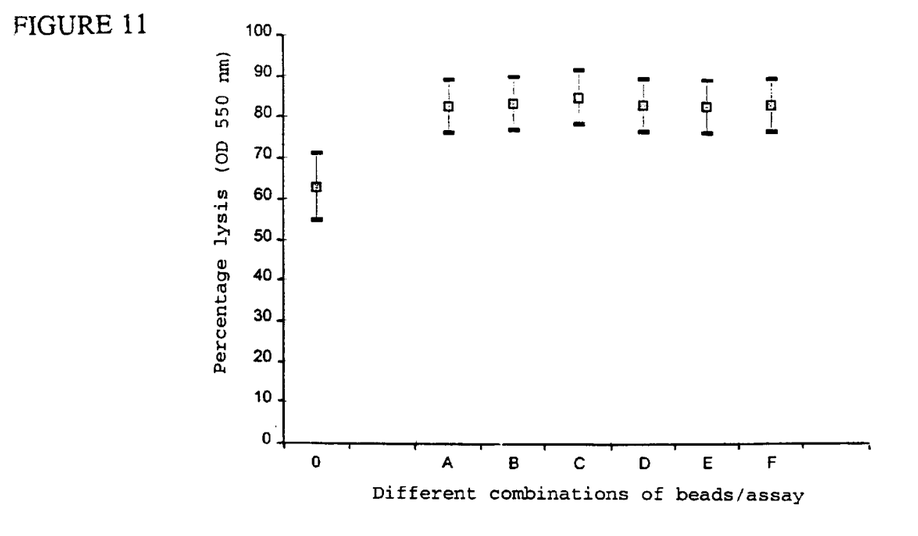
FIG. 11 illustrates the percentage lysis (on the y-axis) as a function of combinations of different beads added (on the x-axis).

FIG. 10 presents the percentage lysis of *S. epidermidis* as a function of the various combinations of beads added. The addition of iron beads or of glass beads causes an increase in the percentage lysis. This percentage is substantially better in the presence of up to 10 beads/tube. The presence of these 10 beads does not hamper the movement of the beads having a diameter of 100 μm; on the other hand above this value, the movement is hampered. The percentage lysis obtained is higher in the presence of the same number of glass beads per experiment as iron beads. According to FIG. 11, the addition of a combination of iron and glass beads makes it possible to obtain a percentage lysis which is as high as in the presence of the addition of a homogeneous mixture of beads for each combination tested; the percentage lysis is greater than 80%. Analysis on 0.8% agarose gel of the nucleic acids released shows that the DNA and rRNA molecules have the same migration profile after lysis regardless of the combinations of beads used. The addition of iron and glass beads does not adversely affect the structure of the nucleic material released. Furthermore, it was verified that their presence in the lysate does not interfere with the PCR and NASBA amplification reactions.

Example 5

Influence of the Vortexing Time on the Efficiency of the Vortex Lysis

Three lysis protocols were performed in parallel:

Protocol I: Eppendorf tube Vc=1.5 ml, 90 μl of beads of diameter 100 μm and 300 μl of cellular suspension α=3.3 and β=5).

Protocol II: protocol I with addition of 3 glass beads of diameter 3 mm and 5 iron beads of diameter 2 mm.

Protocol III: protocol II in a Falcon tube (Vc=6 ml) in place of Eppendorfs.

For each protocol, various vortexing times were performed.

Figure 12:
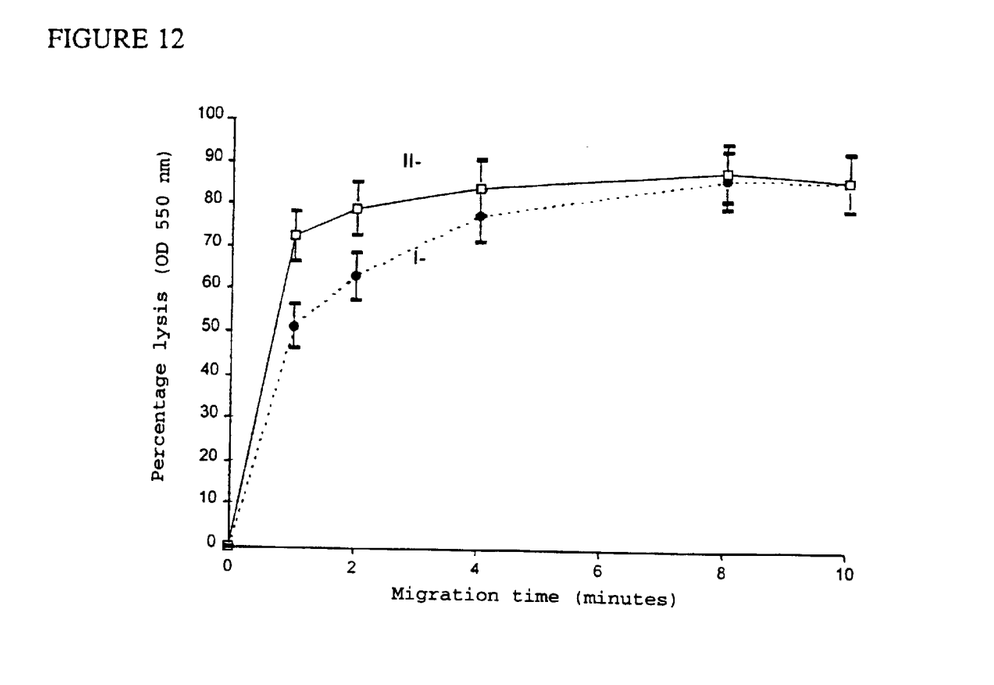
FIG. 12 illustrates the percentage lysis (on the y-axis) as a function of the time for putting through a vortex-type movement (on the x-axis) for the protocols I and II of Example 5.

FIG. 12 presents the percentage lysis obtained as a function of the vortexing time, for protocols I and II. The experimental conditions for protocol I are not optimum. It is confirmed that after 2 minutes of vortexing, only 60% of the *S. epidermidis* bacteria are lysed. On the other hand, it is possible to improve the efficiency of the protocol in spite of these non-optimum conditions by increasing the vortexing time: above 8 minutes of vortexing, 85% of the bacteria are lysed. The experimental conditions for protocol II are more optimum than those for protocol I, due to the addition of beads having a diameter of 3 mm: under these conditions, 85% of the *S. epidermidis* bacteria are lysed above 4 minutes of vortexing.

Figure 13:
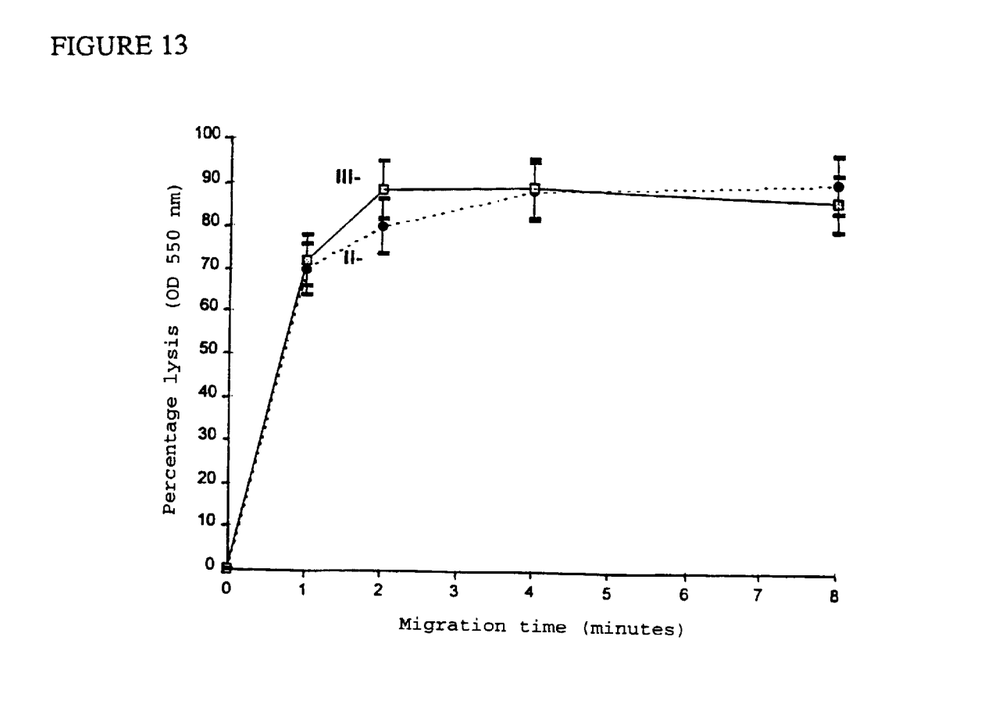
FIG. 13 illustrates the percentage lysis (on the y-axis) as a function of the time for putting through a vortex-type movement (on the x-axis) for the protocols II and III of Example 5.

FIG. 13 presents the percentage lysis obtained as a function of the vortexing time for protocols II and III. The experimental conditions for a protocol III are more optimal than those for protocol II: 88% of the *S. epidermidis* bacteria are lysed after only 2 minutes of vortexing whereas only 80% or 60% of the bacteria after 2 minutes with protocol II or I, respectively. Measurement, by Vidas analysis, of the nucleic acids released confirms these principal observations.

Thus, increasing the vortexing time makes it possible to obtain a high percentage lysis when the initial experimental conditions are not optimum. In parallel, when these conditions are optimum, the vortexing time may be short (2 minutes).

Example 6

Universality of the Lysis Protocol According to the Invention

The lysis method according to the invention may be applied to other cellular species. For that, the protocol was carried out in an Eppendorf tube in the presence of 300 µl of cellular suspension having a concentration of 1×10$^9$ cells/ml, of 90 µl of beads having a diameter of 100 µm with a vortexing time equal to 8 minutes. Various cells were respectively used (*Mycobacterium gordonae, Escherichia coli, Listeria monocytogenes, Streptococcus pneumoniae, Bacillus stearothermophilus, Micrococcus sp., Actinomryces viscosus, Actinomyces naeslundii, Stomatococcus mucilaginosus, Nocardia asteroides, Rhodococcus sp.*) The results obtained indicate that the percentage lysis for each of these analyses is between 80 and 90%. The migration profiles on 0.8% agarose gel of the nucleic acids released in each lysate are similar for each bacterial strain tested, and are similar to that of the purified and commercially available *E.coli* 16S rRNA and DNA.

Example 7

Lysing of Yeast

Species tested: Candida albicans

Container: polypropylene Falcon tube of Vc=6 ml.

Sample adjusted to 0.5 McFarland, that is 3.106 yeasts/ml.

Sample volume: Ve=600 µl

Apparent volume of the beads: Vb (µl, varible): 60, 90 and 180 µl.

Diameter of the glass beads tested (µ):100, 500 and 1500 µm.

The lysis efficiency is measured based on the percentage lysis:

% lysis=OD550 (before lysis)—OD550 (after lysis)/OD550 (before lysis)

Duration of vortexing: 2 to 20 min

Results

| Bead diameter (µ) | Vb (µl) | Duration of vortexing (min) | % lysis |
|---|---|---|---|
| 100 | 90 | 2 | 0 |
| 100 | 90 | 8 | 0 |
| 1500 | 90 | 2 | 0 |
| 1500 | 90 | 8 | 30 |
| 1500 | 90 | 20 | 36 |

It is demonstrated that a diameter of 100 µm is insufficient.

| Bead diameter (µ) | Vb (µl) | Duration of vortexing (min) | % lysis |
|---|---|---|---|
| 1500 | 180 | 8 | 30 |
| 1500 | 180 | 20 | 29 |
| 1500 | 60 | 8 | 33 |

It is demonstrated that with a bead diameter of 1500 µm, a percentage lysis of about 30% is obtained, for a Vb of between 60 and 180 µl and with a vortexing duration of between 8 and 20 min.

| Bead diameter (µ) | Vb (µl) | Duration of vortexing (min) | % lysis |
|---|---|---|---|
| 500 | 60 | 8 | 52 |
| 500 | 60 | 20 | 58 |
| 500 | 180 | 20 | 71 |

It is demonstrated that a diameter of 500 µ makes it possible to obtain a percentage lysis of more than 50%, with a Vb of 60 to 180 µl and a vortexing duration of 8 to 20 min.

Conclusion:

Beads of 500 µm in diameter, with a vortexing duration of between 8 and 20 min are necessary as a parameter in combination with the vortex-type movement for lysing yeasts.

Example 8

Sensitivity of the Lysis Protocol According to the Invention

The DNA and 16S rRNA nucleic acids released by lysis according to the method of the invention were subjected to amplification. The lysis conditions are the same as those indicated in Example 6. The bacterial strain used is *S. epidermidis*. Two amplification protocols specific for *S. epidermidis* nucleic acids were performed starting with the lysates collected, either a PCR protocol for the amplification of the DNA, or an NASBA protocol for the amplification of the 16S rRNA, as described above in the general test protocol.

1)—PCR Amplification of the DNA Released

Initial concentrations of $1\times10^9$ to $1\times10^2$ cells/ml were used. 10 µl of lysate were used for each PCR assay. The amplicons produced were detected and quantified after specific sandwich hybridization on Vidas apparatus, as described in the general test protocol. The amplicons produced can be measured for initial bacterial concentrations at least greater than or equal to $1\times10^2$ cells/ml, that is 30 cells/300 µl. Thus, the optimized lysis protocol by vortexing is effective for lysing at least 30 cells/300 µl and for releasing DNA molecules which can be amplified by PCR such that the quantity of amplicons produced is detectable.

2)—NASBA Amplification of the 16S rRNA

Initial concentrations of $2\times10^9$ to $2\times10^2$ cells/ml were used. 5 µl of lysate were used for each NASBA assay. The amplicons produced were detected and quantified on microplate by sandwich hybridization with oligonucleotide probes specific for *S. epidermidis*, as described in the general test protocol. The amplicons produced could be detected and measured for initial bacterial concentrations at least greater than or equal to $2\times10^2$ cells/ml, that is 60 cells/300 µl. The quantity of amplicons measured is high for this initial concentration, which indicates that probably amplicons produced after lysis of bacteria having an initial concentration of less than 60 cells/300 µl would be detectable and measurable.

Example 9

Resolution of the Formation of Foam Resulting From the Shaking of Beads in a Sample For the purposes of automation, it is essential to resolve and prevent the formation of foam in the liquids, which interferes with or even prevents the steps of transferring via pipetting. "Antifoaming" agents were studied with respect to their capacity to limit this type of phenomenon. To do this, a protocol was validated using respiratory samples (sputum, expectorations, bronchoalveolar washings) which have been made fluid and inactivated according to the "NaLc" protocol. Briefly, 2 ml of sample are added to 2 ml of antiseptic solution (obtained by dissolving 0.75 g of N-acetyl-L-cysteine in 150 ml of 4% sodium hydroxide). The mixture is vortexed and kept stirring for 20 minutes at room temperature, and then neutralized with 41 ml of phosphate buffer (pH 6.8). The whole medium is vortexed for 50 seconds and then centrifuged at 4° C. for 25 minutes at 4000 g. The pellet is resuspended (vortex, 15 seconds) in 2 ml residuals after having eliminated the supernatant.

Various samples are then mixed in order to have a homogeneous and consistent medium for the study. The experiments are carried out in the following manner: 260 µl of samples are added to a 12×75 mm polypropylene tube with 90 µl of glass beads having a diameter of 100 µm, 3 glass beads having a diameter of 2 mm, 5 iron beads having a diameter of 2 mm. 40 µl of an anionic detergent are added in order to obtain a final concentration of 2.5%. The presence of a detergent is justified by the fact that the nucleic acids are stabilized and protected during the lysis process.

The whole medium is stirred in a Reax 2000 vortex (Heidolph) at the maximum power for 12 minutes (time which is particularly long compared with the standard protocol, but which should promote the possible formation of foam where appropriate). The height of the liquid in the tube is measured initially and then after stirring and the percentage of foam obtained is expressed in the following results by calculating the ratio of the height of the foam to the initial height.

TABLE N

| Antifoam concentration (%) | Generation of foam (%) |
|---|---|
| 0 | 22% |
| 0.01 | 11% |
| 0.03 | 11% |
| 0.1 | 11% |
| 0.5 | 0% |
| 1% | 0% |

The antifoaming agent, in particular Foam Ban MS-575 (Ultra Inc., Charlotte, USA) is added in a negligible volume, in order to obtain final concentrations of 0.01 to 1% (Table N).

The results (see Table N) show that the presence of an antifoam allows the resolution of the formation of foam, in particular from clinical samples such as sediments. Its use at a concentration of 0.5 to 1% makes it possible to completely resolve the formation of foam resulting from the stirring of the liquid sample in the presence of beads.

The efficiency of the antifoam was also verified using individual samples (not mixed), at the final concentration of 0.6%, according to the protocol described above.

The results (see Table N+1) show that the formation of foam is variable according to the biological samples, but that the presence of antifoam in the lysis protocol resolves and prevents the formation of foam from various respiratory samples.

TABLE N + 1

| | Generation of foam (%) | |
|---|---|---|
| Sample | with foam | without foam |
| 2675 6/2 | 0% | 16% |
| 2677 6/2 | 0% | 16% |
| 2654 6/2 | 0% | 16% |
| 2673 6/2 | 0% | 22% |
| 3609 71 | 0% | 11% |
| 3673 92 | 0% | 16% |

Example 10

Sensitivity of the Protocol for Lysing Microorganisms in the Presence of Antifoaming Agents The efficiency of the whole lysis protocol, in particular in the presence of antifoam, was evaluated on samples containing very low concentrations of bacteria. The bacteria *Mycobacterium bovis* BCG was used, because this *Mycobacterium* genus is known to be difficult to lyse, and is particularly tested for in respiratory specimens.

Serial dilutions, starting with a homogeneous initial suspension of bacteria whose concentration was determined by densitometric measurement (optical density at 550 nm), were made in order to inoculate in a negligible volume fractions of sediment which is negative (reconstituted by mixing various fluidified and decontaminated negative sediments) and inactivated sediment (heating at 95° C. for 15 minutes). The samples thus reconstituted were subjected to the following protocol:

dilution in a buffer containing an anionic detergent and Foam Ban MS-575 antifoam in order to obtain concentrations of 2.5% and 1% final, respectively.

heating at 95° C. for 15 min (inactivation of the bacteria).

a volume of 600 µl is added to the 12×75 mm cell (polypropylene) containing 180 µl of glass beads of 100 µm, 6 glass beads (diameter 2 mm), 10 iron beads (diameter 2 mm) and the whole medium is shaken with the aid of a vortex for 2 minutes at the maximum power.

In parallel, control experiments are carried out: these are subjected to the same protocol as described above except the step of shaking the beads by vortexing.

The nucleic acids thus potentially released are then purified by a specific capture step on magnetic beads (Seradyne) derivatized with a capture oligonucleotide which is complementary to the *M. tuberculosis* BCG 16S RNA sequence, according to the following protocol:

- 250 µl of lysate obtained are mixed with a capture buffer containing the oligonucleotide probes coupled to magnetic beads (50 µg/assay). The whole medium is incubated for 20 min at 60° C., then for 10 min at room temperature, and then the supernatant is eliminated after immobilizing the beads on the walls of the tube by magnetization.
- the beads are washed (resuspension and then magnetization) with 2 fractions of 1 ml of washing buffer.
- after elimination of the buffer, the beads are resuspended with 50 µl of water and 25 µl of the amplification mixture containing oligonucleotide primers and deoxyribonucleotides of the *M. tuberculosis* identification kit ("Amplified Mycobacterium Tuberculosis Direct", Gen-Probe ref. 1001), which is based on "Transcription-Mediated Amplification" (TMA), described by McDonough et al. (Nucleic Acids Amplification Technologies, 1997, Ed. Lee, Morse & Olsvik, Eaton Publishing, Natik, USA, pp. 113–123) as well as Kacian and Fulz (Nucleic Acid Sequences Amplification Methods, 1995, U.S. Pat. No. 5,399,491).
- the whole medium is heated at 60° C. for 15 min, cooled at 42° C. for 5 min, and 25 µl of the enzymatic solution of the kit (containing T7 RNA polymerase and reverse transcriptase) are added.
- the reaction is incubated for 1 hour at 42° C. and then analyzed using the detection reagents of the kit, according to the "Hybridization Protection Assay" (HPA) technique described by Arnold et al. (Clin. Chem., 1989, Vol. 35, pp. 1588–1594).

The reactions are then read on a 450 i luminometer (Gen-Probe) and result in data in relative light units (RLU), the limit of positivity of an assay being 30,000 RLUs.

The data obtained are indicated in Table N+2, and correspond to three experimental assays per conditions tested.

TABLE N + 2

| Bacteria/assay | $10\ \text{Exp} - 3$ | $10\ \text{Exp} - 1$ | $10\ \text{Exp} + 1$ | $10\ \text{Exp} + 3$ | |
|---|---|---|---|---|---|
| Without vortexing | 415 | 402 | 508 | 119736 | |
| | 467 | 554 | 422 | 2312 | |
| | 371 | 364 | 179756 | 1013140 | |
| | 418 | 440 | 60229 | 378396 | Mean |
| | 48 | 101 | 103514 | 552831 | Standard deviation |
| | 12 | 23 | 172 | 146 | Co-efficient of variation (%) |
| With vortrexing | 43117 | 457 | 1029901 | 1079399 | |
| | 1088 | 919609 | 125 | 1030602 | |
| | 389 | 453 | 1069273 | 1058371 | |
| | 144198 | 306840 | 700100 | 1056124 | Mean |
| | 248479 | 530674 | 605650 | 24476 | Standard deviation |
| | 172 | 173 | 87 | 2 | Co-efficient of variation (%) |

The results (see Table N+2) show that carrying out the lysis protocol using glass beads in the presence of antifoaming agents makes it possible to detect in the biological samples a quantity equivalent to $10^{-3}$ bacteria/assay, that is a quantity equivalent to 1 to 10 of ribosomes in a sensitive manner. By comparison, the absence of lysis (except initial heating in the presence of detergent for the inactivation of the samples) can only detect the equivalent of 10 to 1000 bacteria per assay, that is 10,000 times less than with the lysis method used.

These results show the validity of the protocol associating the lysing of bacteria by mechanical shock in the presence of beads (with the aid of a vortex and the like) combined with the use of antifoaming agents. The combination of a method of lysis by the shaking of beads is therefore perfectly appropriate.

What is claimed is:

1. Method of lysing a biological sample comprising at least one microorganism, in order to release at least one nucleic material of interest belonging to said microorganism, said microorganism being of a bacterium type or a yeast type, wherein:

said biological sample in a liquid medium is placed in a container, at least one particulate material which is substantially inert relative to the nucleic material is placed in said container, the mixture of biological sample and particulate material is subjected to a movement, whereby, in combination:

the particulate material consists of beads having a diameter ranging from 90 $\mu$m to 150 $\mu$m when said microorganism is of the bacterium type, and having a diameter of about 500 $\mu$m when said microorganism is of the yeast type, and the movement chosen is of the vortex type, and corresponds to the following conditions:

the apparent volume of the beads, Vb, and the volume of the liquid sample, Ve, are linked by the relationship Ve=$\alpha \times$Vb, wherein Vb<Ve, with a between 1.4 and 10 when the container is in tubular form, and $\alpha$ less than or equal to 2.1 when the container is in disk form, whereby, without one or more additional operating steps, the nucleic material is released directly into the liquid medium in the native state and in a state accessible to any reagent for subsequent treatment.

2. Method according to claim 1, wherein said microorganism is of the bacterium type.

3. Method according to claim 1, wherein said microorganism is of the yeast type.

4. Method according to claim 2, characterized in that the particulate material consists of beads having a diameter of about 100 $\mu$m.

5. Method according to claim 2, characterized in that the vortex-type movement satisfies, in addition, the following relationship:

Vb<Ve<Vc, according to which

Vc=$\beta \times$Ve, and $\beta$ is a number between 2.5 and 30, Vc being the useful volume of the container.

6. Method according to claim 2, characterized in that the container is in tubular form.

7. Method according to claim 6, characterized in that the container has a U-shaped bottom.

8. Method according to claim 5, whereby the container is a tube with a frustoconical bottom, and $\alpha$ is a number between 1.4 and 3.3, and $\beta$ is a number between 2.5 and 15.

9. Method according to claim 5, whereby the container is a tube with a U-shaped bottom, and $\alpha$ is a number between 1.4 and 3.3, and $\beta$ is a number between 3 and 30.

10. Method according to claim 5, whereby the container is in disk form and $\alpha$ is less than or equal to 1.4 and $\beta$ is greater than or equal to 9.3.

11. Method according to claim 2, characterized in that the particulate material further comprises other beads having a diameter greater than that of said beads.

12. Method according to claim 11, characterized in that the container further comprises up to 16 other beads having a diameter equal to about 2 to 3 mm.

13. Method according to claim 12, wherein number of the other beads is up to 10.

14. Method according to claim 2, characterized in that an antifoaming substance is added to a final concentration of 0.01 to 1% of the volume of the liquid sample, Ve.

15. Method according to claim 14, characterized in that a detergent of the anionic type is in addition added to a final concentration of 2.5% of the volume of the liquid sample, Ve.

16. Method according to claim 2, characterized in that the time for putting through a vortex-type movement is at least equal to 10 seconds.

17. Method according to claim 16, characterized in that the time for putting through a vortex-type movement is about 2 minutes.

18. Method according to claim 3, characterized in that the time for putting through a vortex-type movement is between 8 and 20 minutes.

19. Method of treating a biological sample comprising at least one microorganism of a bacterium type or a yeast type, comprising a nucleic material of interest, wherein:

said sample is lysed according to the method according to claim 18, the lysed biological sample, with or without the particulate material which served for the lysis, is subjected directly to an operating protocol relating specifically to the nucleic material of interest.

20. Method according to claim 19, wherein the operating protocol is that of nucleic detection or amplification.

* * * * *